(12) United States Patent
Helle et al.

(10) Patent No.: US 8,221,302 B2
(45) Date of Patent: Jul. 17, 2012

(54) SHIELDED CARTRIDGE ASSEMBLY FOR BRACHYTHERAPY SEEDS

(75) Inventors: Kevin Helle, Bartlett, IL (US); Jay Reed, Elk Grove, IL (US); David Anchor, Round Lake Park, IL (US)

(73) Assignee: Medi-Physics, Inc., Princeton, NJ (US)

( * ) Notice: Subject to any disclaimer, the term of this patent is extended or adjusted under 35 U.S.C. 154(b) by 613 days.

(21) Appl. No.: 12/299,499

(22) PCT Filed: May 7, 2007

(86) PCT No.: PCT/US2007/068360
§ 371 (c)(1),
(2), (4) Date: Nov. 4, 2008

(87) PCT Pub. No.: WO2007/134002
PCT Pub. Date: Nov. 22, 2007

(65) Prior Publication Data
US 2009/0069625 A1  Mar. 12, 2009

(51) Int. Cl.
*A61M 36/00* (2006.01)
*A61N 5/00* (2006.01)
(52) U.S. Cl. .......................................................... 600/7
(58) Field of Classification Search ................... 600/1, 7; 604/59
See application file for complete search history.

(56) References Cited

U.S. PATENT DOCUMENTS

| | | | |
|---|---|---|---|
| 2002/0077522 A1 | 6/2002 | Hamazaki et al. | |
| 2002/0120174 A1 | 8/2002 | Steele et al. | |
| 2004/0147800 A1* | 7/2004 | Barber et al. | 600/7 |
| 2005/0267320 A1 | 12/2005 | Barber et al. | |
| 2006/0063960 A1 | 3/2006 | Wissman et al. | |
| 2006/0173236 A1* | 8/2006 | White et al. | 600/7 |

FOREIGN PATENT DOCUMENTS

| | | |
|---|---|---|
| EP | 1072287 | 1/2001 |
| WO | 97/22379 | 6/1997 |
| WO | 01/87406 | 11/2001 |
| WO | 03/063944 | 8/2003 |

OTHER PUBLICATIONS

PCT/US2007/068360 Int'l Search Report/Written Opinion dated Oct. 2007.

* cited by examiner

*Primary Examiner* — John Lacyk
(74) *Attorney, Agent, or Firm* — Robert F. Chisholm (57) ABSTRACT

A brachytherapy seed cartridge assembly includes an elongate movable shield, formed from a radiation-shielding material, that is slideably supported so as to movable between an extended position and a retracted position. The cartridge assembly also provides a quick-connect feature for a more efficient assembly and disassembly.

11 Claims, 7 Drawing Sheets

SHIELDED CARTRIDGE ASSEMBLY FOR BRACHYTHERAPY SEEDS

FIELD OF THE INVENTION

The present invention is directed to the field of devices for brachytherapy. More specifically, the present invention relates to a shielded cartridge assembly for brachytherapy seeds.

BACKGROUND OF THE INVENTION

The art has seen cartridge assemblies in which brachytherapy seeds are loaded prior to shipping and dispensement of the seeds into an elongate cannula, or seed applicator, from which they are then implanted into a patient. Brachytherapy seed cartridges are provided with a number of radioactive brachytherapy seeds, e.g. I-125 or Pd-103 seeds, and used as a supply source of those seeds to be loaded into a seed applicator. FIGS. 1 and 2A-C depict a typical seed cartridge 10 manufactured and sold by Mick Radio-Nuclear Instruments, Inc. of Mount Vernon, N.Y., U.S.A. Cartridge 10 includes a magazine 12 and a cap 14. Magazine 12 includes an elongate seed channel 16 for receiving transversely-aligned brachytherapy seeds 18 and dispense aperture 20 from which the seeds are dispensed into the applicator. Cap 14 supports an elongate plunger 22 which is spring-biased to extend into channel 16 and urge the seeds 18 towards dispense aperture 20. Magazine 12 further includes an external helical thread 24 for mating with an internal helical thread, not shown, within cap 14. Cap 14 includes an external thread 26 to secure the assembled cartridge 10 in a V-block for steam sterilization.

To form a disposable, or single-use, cartridge 10, magazine 12 and cap 14 are typically made of a suitable plastic material capable of withstanding steam sterilization. Alternatively, cap 14 may be formed from stainless steel or brass in order to provide some degree of shielding. This later feature recognizes that a technician holding a cartridge component in each hand while threading the two components together risks radiation exposure which should be minimized further. While a technician can work behind an 1-block type shield, that will only help with body exposure. Hand (extremity) exposure remains high due to the dexterity needed to mate and screw the two parts together, due to the proximity of the radioactive seeds to the technician's hands and fingers.

As the cartridge assembly contains radioactive seeds it is extremely important to consider radiation shielding. Shielding is considered important from a manufacturing perspective; ALARA (As Low As Reasonably Achievable) is a commonly used acronym to ensure employee radiation exposure is reduced by means of procedure, controls and personal protective equipment. Shielding is also an extremely important aspect of marketing a radioactive source, such as a seed. Manufacturers that consider occupational exposure to their products, and the reduction thereof, are being proactive in distributing the safest product possible. Shielding of this product would offer lower occupational exposure levels to physicians and their staff in the clinical use of the product. The cartridge assemblies currently used expose the user or handler to radiation immediately adjacent the seeds as well as along the line of sight to any visible (unshielded) seeds.

In addition to shielding it is very important to consider the time of exposure to a radiation source. This aspect relates both to the manufacturing assembly of the loaded cartridge as well as to the event where an end user disassembles and then re-assembles a cartridge. The currently-used cartridge assemblies are threaded together at the top and bottom. To join or disassemble the two parts requires time and also a bit of dexterity as the mating threads may require up to seven full revolutions of the component parts. During the whole process the technician will be exposed to the radiation of the seeds. Moreover, in the event of mal-assembly such as cross threading, the plastic magazine 12, with the seeds loaded into it, may become damaged and cause both a longer period of exposure to the technician and a loss of the cartridge assembly.

The existing cartridge assemblies are described and marketed as being shielded and disposable, but only provide shielding in a portion of the cartridge areas. There is therefore a need for a brachytherapy seed cartridge assembly that will greatly reduce, or even eliminate, radiation exposure to the users and handlers of the cartridge during loading, transportation, and use.

SUMMARY OF THE INVENTION

In view of the needs of the prior art, the present invention provides a brachytherapy seed cartridge assembly having an elongate movable shield, formed from a radiation-shielding material, that is slideably supported so as to movable between an extended position and a retracted position. The cartridge assembly includes an elongate cartridge body defining first and second transversely-opposed openings, a first open end, and an elongate seed passageway extending therebetween. In the extended position, the movable shield extends about the seed passageway of the cartridge body, preferably also about the first and second transversely-opposed openings.

DETAILED DESCRIPTION OF THE PREFERRED EMBODIMENT

With reference to FIGS. 3, 4, 17 and 18, the present invention provides a brachytherapy seed cartridge assembly 110. Cartridge assembly 110 includes an elongate cartridge body 112, an elongate housing body 114, and a movable shield 116 which is movable between an extended position and a retracted position. Cartridge body 112 receives, holds, and allows dispensing of a plurality of transversely-arrayed brachytherapy seeds 115. Cartridge assembly 110 desirably includes a fixed shield 118 at a free end 120 of cartridge body 112.

While the present invention contemplates that only shield 116 is formed from a radiation-shielding material, it is further contemplated that housing body 114 and fixed shield 118 are desirably also formed from a radiation-shielding material. It is further contemplated that shield 116, in the extended position, extends about the brachytherapy seeds held within housing body 114, and desirably is positionable so as to extend about at least a portion of fixed shield 118.

Figure 1:
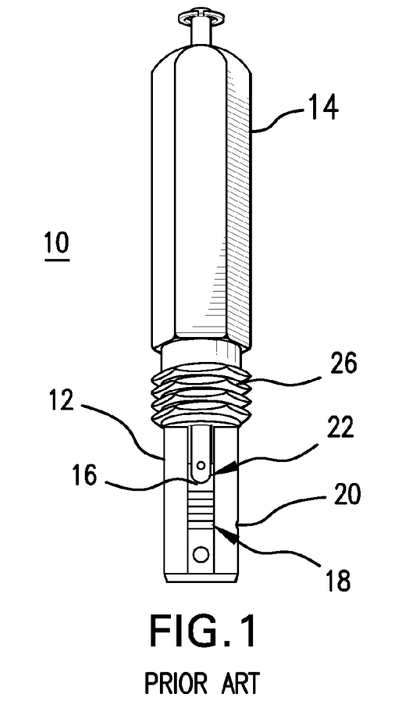
FIGS. 1 and 2A-C depict a brachytherapy seed cartridge assembly of the prior art.
Figure 2A:
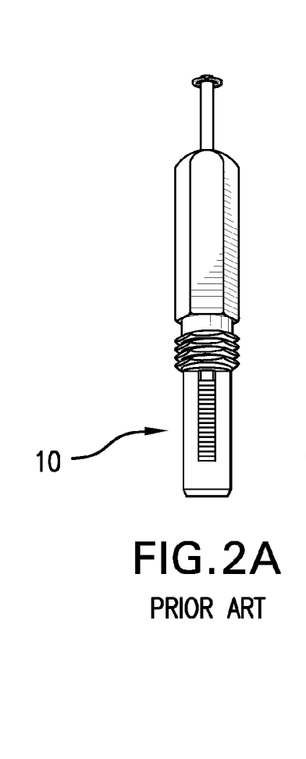
Figure 2B:
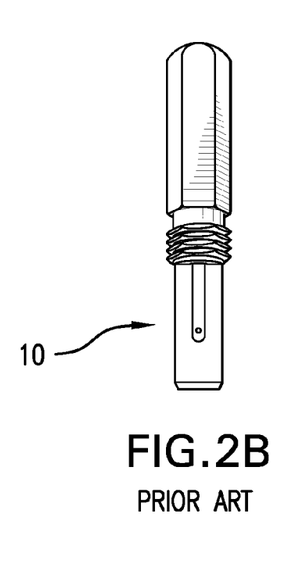
Figure 2C:
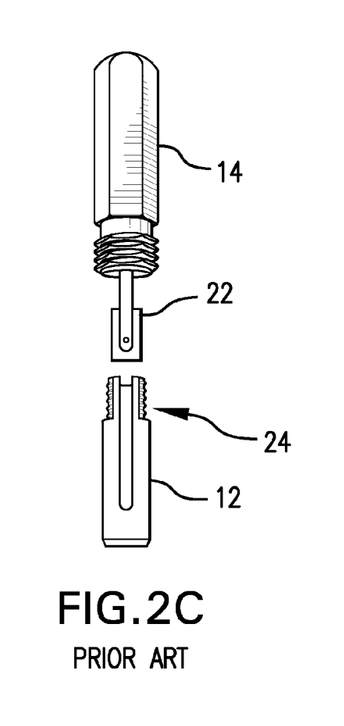
Figure 3:
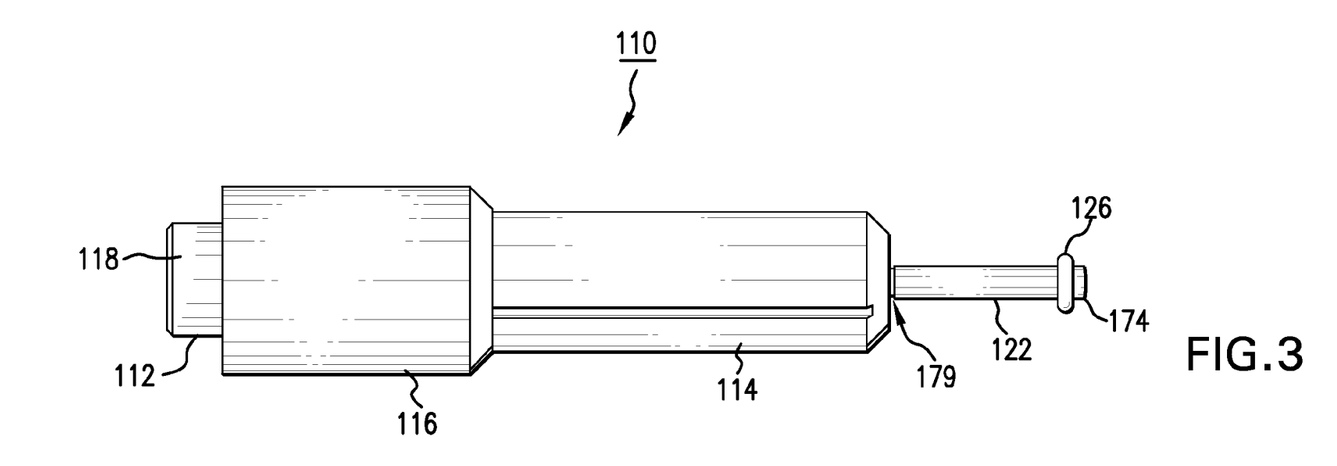
FIG. 3 shows a brachytherapy cartridge assembly of the present invention, showing the shield of the cartridge in the lowered position.
Figure 4:
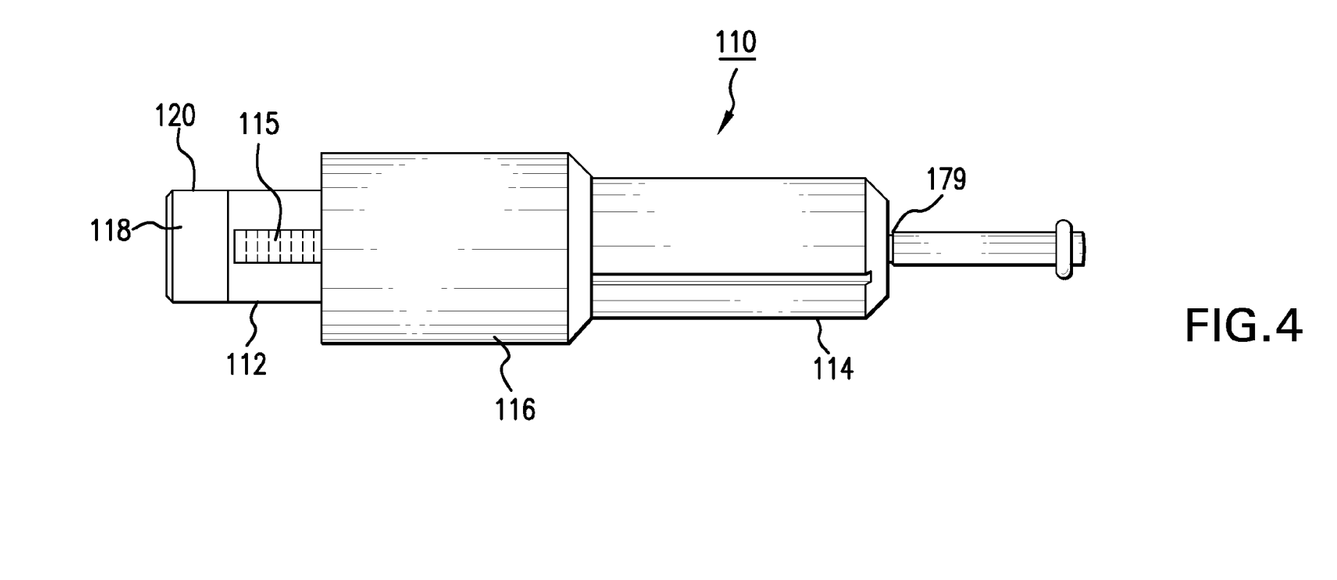
FIG. 4 depicts the cartridge assembly of FIG. 1, with the shield in the raised position.
Figure 5:
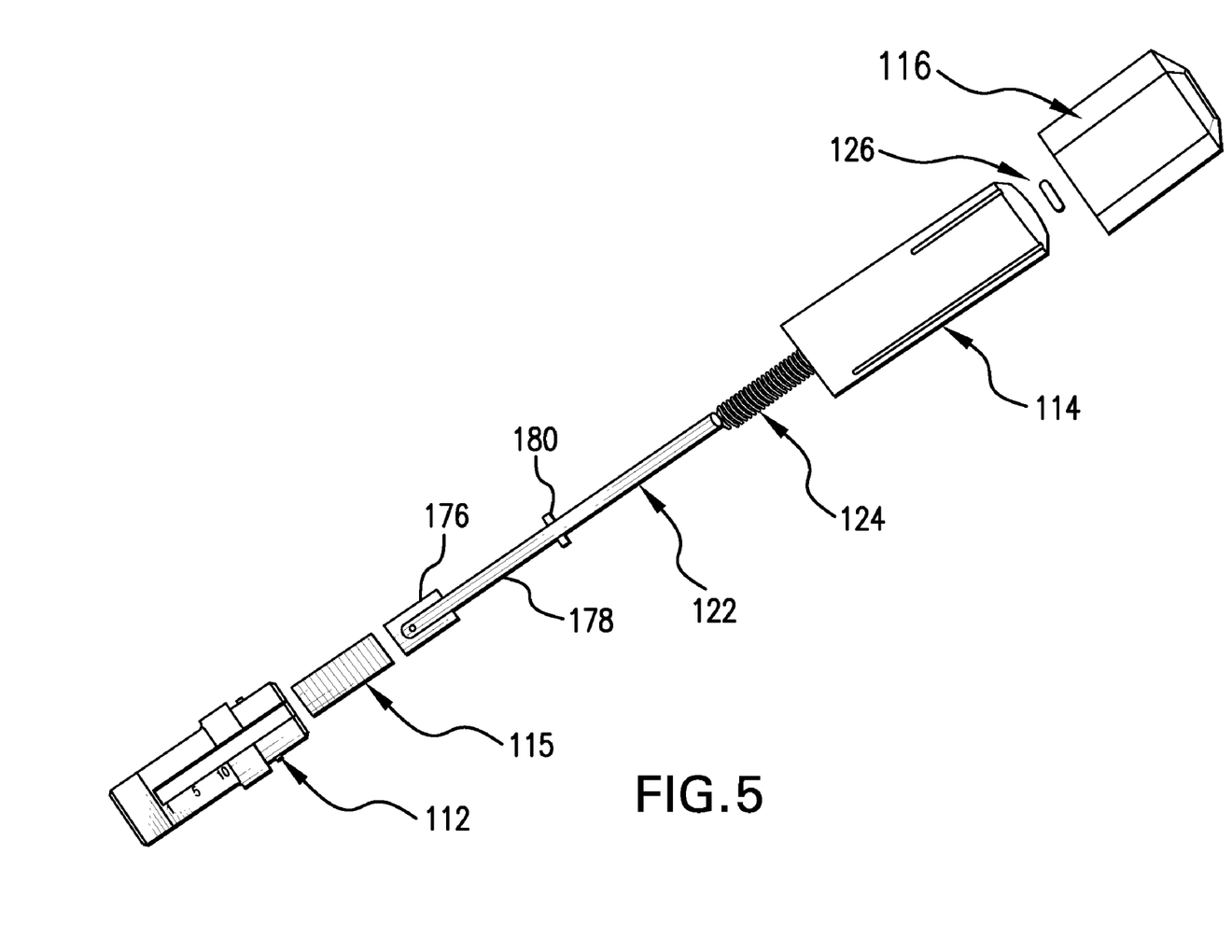
FIG. 5 depicts an exploded view of the cartridge assembly of the present invention.
Figure 6:
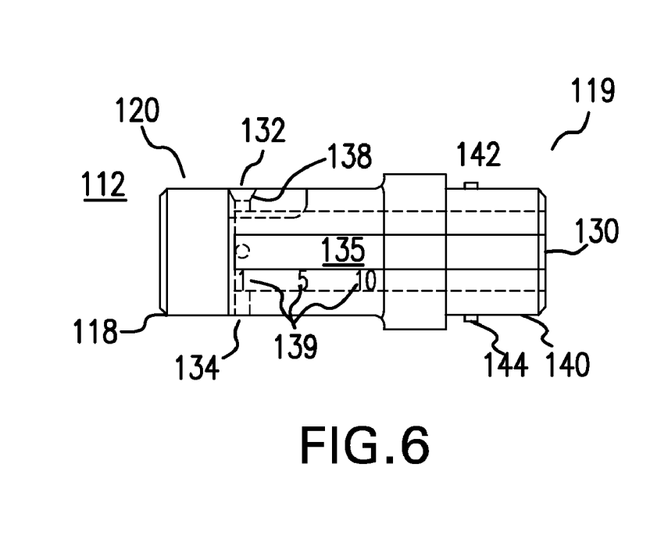
FIGS. 6-9 show several views of the cartridge body of the present invention.
Figure 7:
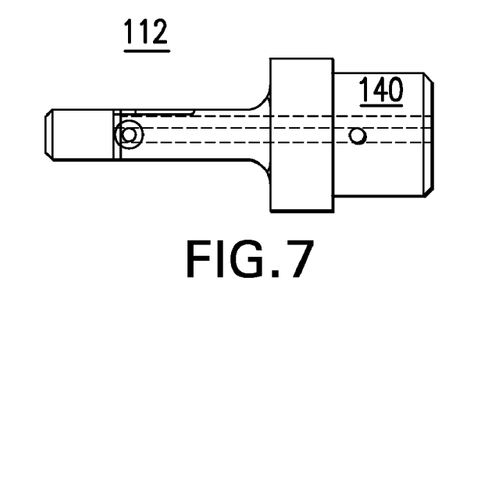
Figure 8:
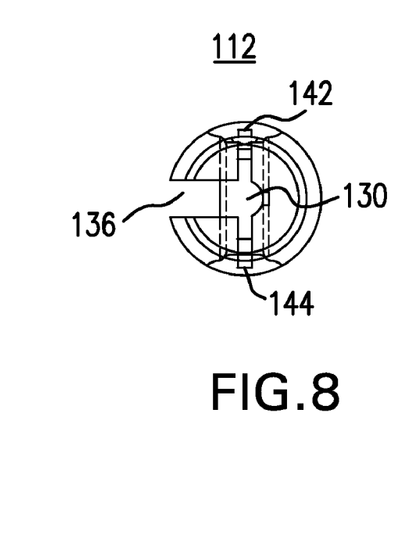
Figure 9:
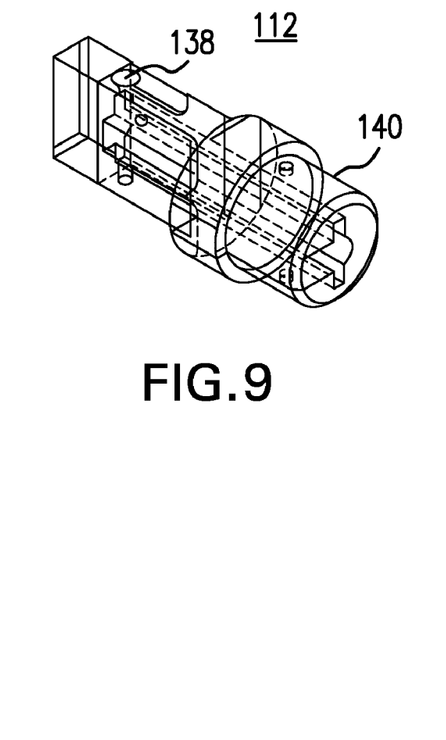
Figure 10:
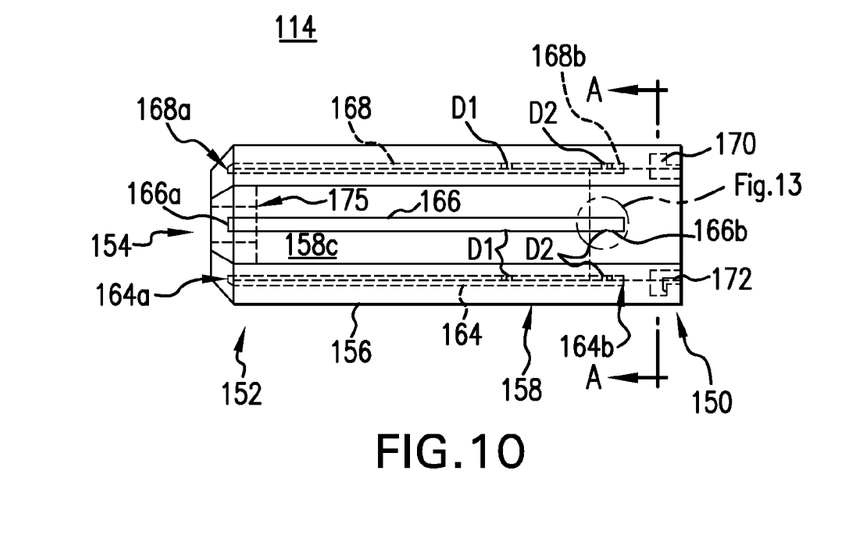
FIGS. 10-13 show several views of the housing body of the present invention.
Figure 11:
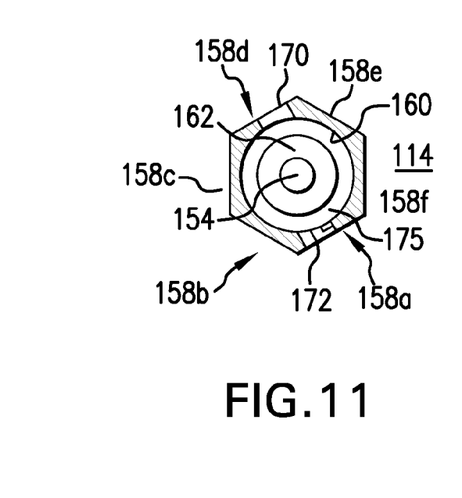
Figure 12:
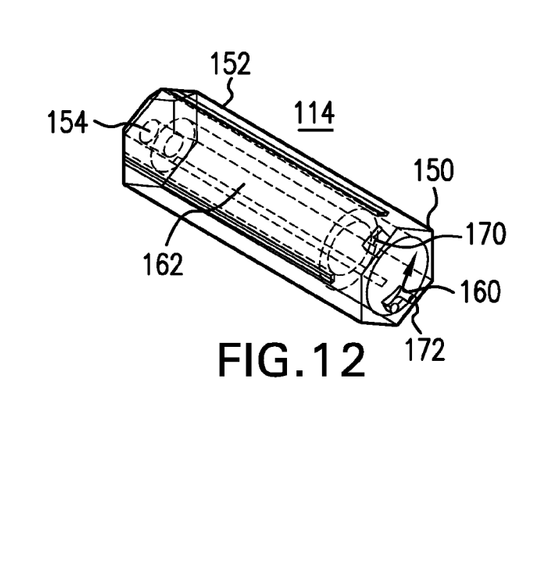
Figure 13:
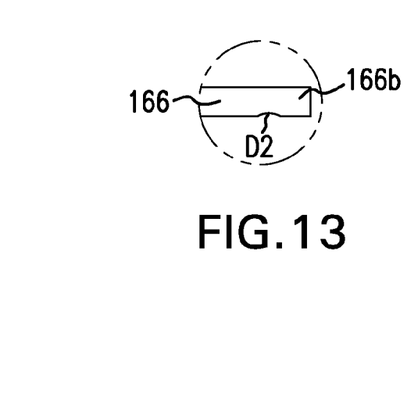

As shown in FIG. 5, cartridge assembly 110 also includes an internally-supported elongate plunger 122, a spring 124 for biasing plunger 122 against an internal surface of housing 114, and an elastomeric O-ring 126 which is supported about one end of plunger 122.

FIGS. 6-9 provide greater detail on cartridge body 112. Cartridge body 112 has a first end 119 and a second end 120. First end 119 defines an input opening 130 while second end 120 defines first opening 132 and second, transversely opposing opening 134. Cartridge body 112 defines an elongate seed passageway 135 extending in fluid communication between input opening 130 and first and second transversely-opposed openings 132 and 134. Cartridge body 112 further defines an elongate access channel 136 in overlying fluid communication with seed passageway 135 so as to allow a technician to have access to manipulate any seeds within passageway 135. Numerical indicia 139 are provided on cartridge body 112 adjacent to access channel 136 so as to correspond to the number of seeds loaded within seed passageway 135. Numerical indicia 139 provide a quick visual reference to a technician attempting to verify the number of seeds currently loaded in cartridge body 112. First opening 132 is further defined by a frustro-conical wall 138 which acts to guide a dispense rod therethrough to push a loaded seed out through second opening 134.

Second end 120 of cartridge body 112 supports fixed shield 118 thereon. Fixed shield 118 is desirably formed from nickel-plated brass. Fixed shield 118 is desirably overmolded onto second end 120 of cartridge body 112 or adhered thereto using suitable adhesive material. First end 119 further includes a cylindrical exterior wall 140 supporting oppositely-extending first and second locking tabs 142 and 144. Cylindrical wall 140 and locking tabs 142 and 144 cooperatively engage housing body 114 so as to hold the two components together.

Referring now to FIGS. 10-13, elongate housing body 114 includes a first open end 150 securable to first open end 119 of cartridge body 112, a second end 152 defining a plunger aperture 154, and an elongate cylindrical wall 156 extending between first open end 150 and second end 152. Cylindrical wall 156 includes outer surface 158 and inner surface 160. Outer surface 158 is desirably multi-faceted to facilitate finger engagement for connecting housing body 114 to cartridge body 112. In this embodiment, outer surface 158 forms a hexagonal surface with facets 158a-f. Inner surface 160 is desirably cylindrical in shape and defines a housing cavity 162 extending in fluid communication between first open end 150 and plunger aperture 154.

Facets 158a, 158c, and 158e define elongate longitudinal channels 164, 166, and 168, respectively. Each of channels 164, 166, and 168 include an open first end 164a, 166a, and 168a as well as a closed second end 164b, 166b, and 168b. Additionally, one or more of channels 164, 166, and 168 include restrictive detents D1 and D2 narrowing the transverse dimension of the channel so as to secure the moveable shield 116 in either the extended or retracted position, as further described below.

Figure 17:
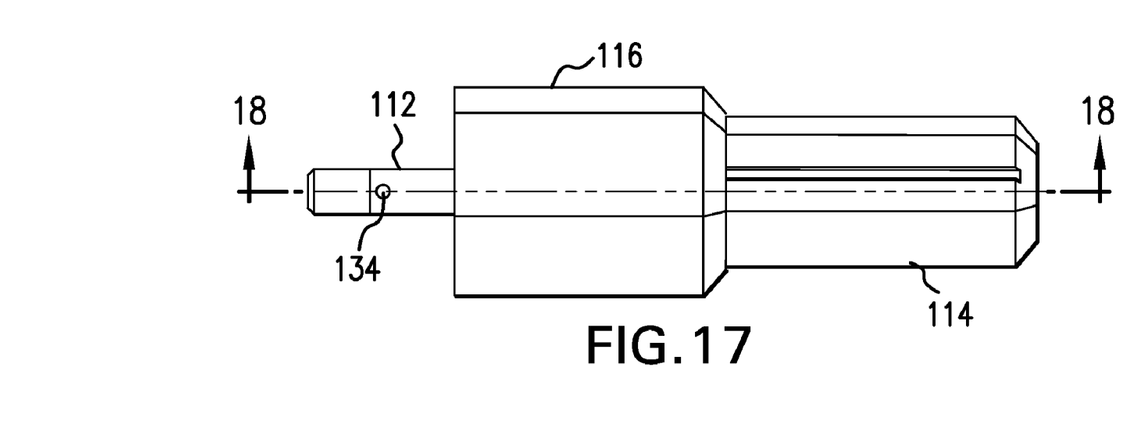
FIG. 17 depicts the cartridge assembly of the present invention with its plunger snapped at its weakened portion.
Figure 18:
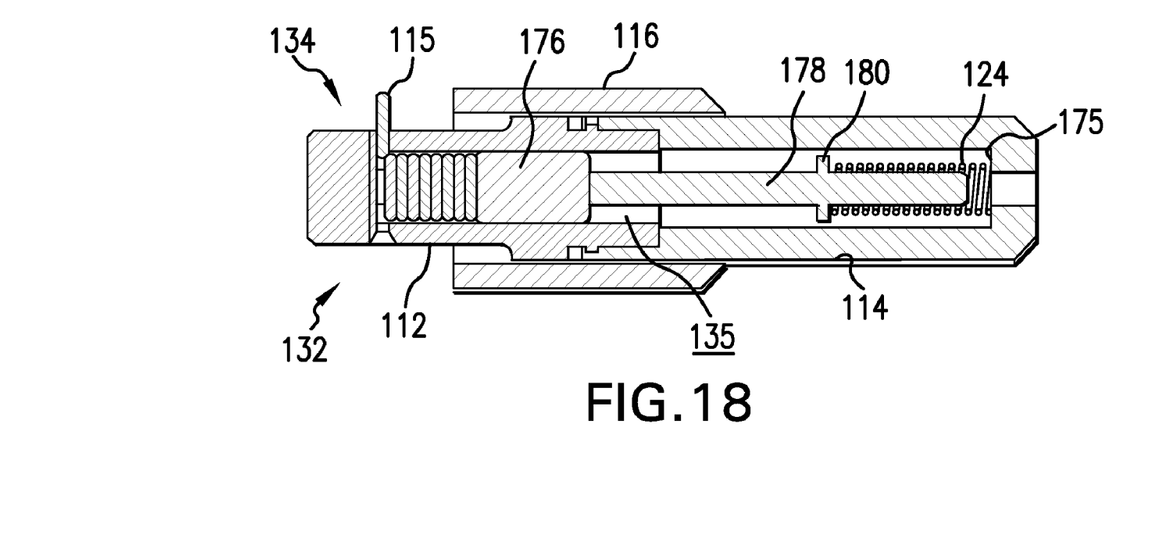
FIG. 18 depicts a cross-sectional view of the cartridge assembly of the present invention taken through the line 18-18 of FIG. 17.

Second end 152 of housing body 114 includes transversely-extending cap surface 175 against which one end of spring 124 will abut, as better shown in FIG. 17. Inner surface 160 also defines a first and second J-slot 170 and 172 opening on first end 150 of housing body 114. J-slots 170 and 172 accommodate first and second locking tabs 142 and 144 so that a simple insertion and twist motion will secure housing body 114 to cartridge body 112.

With additional reference to FIGS. 3, 5, 17 and 18, plunger 122 includes a first end 174, a second end 176 and an elongate plunger body 178 extending therebetween. Second end 174 supports O-ring thereon. Should cartridge assembly 110 be shipped within a Tyvek primary sterility barrier bag container, the provision of O-ring 126 will cause less damage to the container wall than the currently-used metallic E-rings. Plunger body 178 desirably includes a score 179 to render plunger body 178 frangible at that point. Once cartridge 110 is loaded and assembled, a technician may apply a breaking force to second end 174 so as to snap off the excess length of plunger 122. The location of score 179 desirably corresponds to the second end of housing body 114 when seed passageway contains the desired number of seeds therein and plunger 122 is thereby retracted. Breaking of the plunger at score 179 shortens the shipping size of cartridge assembly 110, ensures that cartridge assembly 110 is truly a single-use device, and completely eliminates the potential for sterility breach of the primary package.

Plunger body 178 includes a spring-engaging tab 180 for abutting engagement with one end of spring 124. Compression of spring 124 between tab 180 on plunger 122 and surface 175 of housing body 114 in the assembled cartridge 110 will urge first end 174 of plunger 122 towards openings 132 and 134. Any seeds 115 loaded within seed passageway 135 will thus be advanced towards a position to be dispensed from opening 134.

Figure 14:
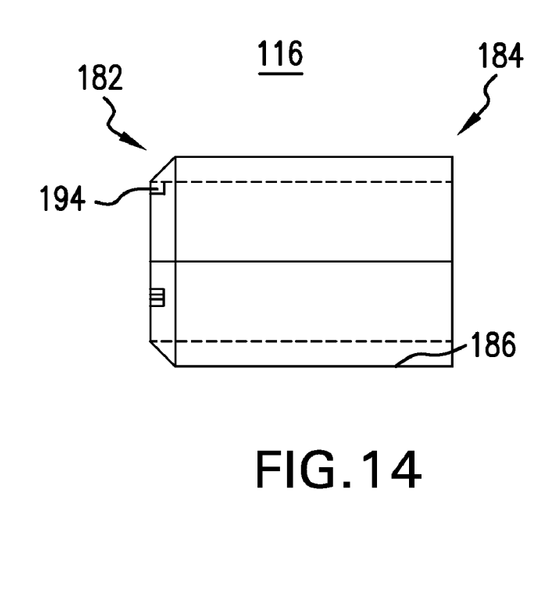
FIGS. 14-16 show several views of the shield of the cartridge of the present invention.
Figure 15:
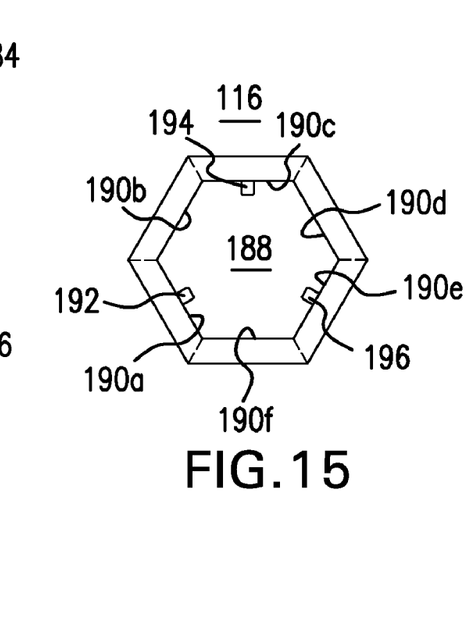
Figure 16:
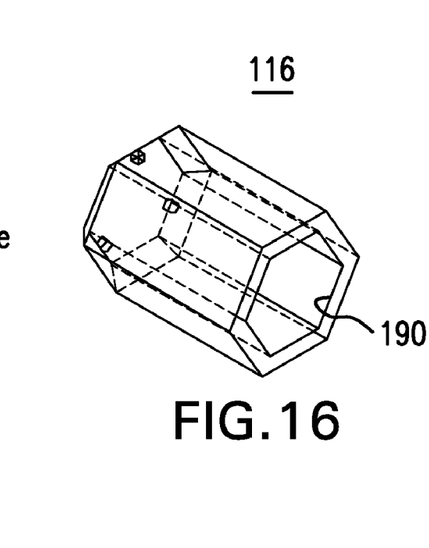

FIGS. 14-16 depict moveable shield 116 in greater detail. Shield 116 is formed from a radiation-shielding material and is shaped to slide over housing body 114 and cartridge body 116. Shield 116 includes a first open end 182, a second open end 184 and an elongate shield wall 186 extending therebetween. Shield wall 186 defines an elongate shield passageway 188 in fluid communication between open ends 182 and 184. Shield wall 186 includes a hexagonally-shaped inner surface 190 having facets 190a-f. Facets 190a-f correspond to facets 158a-f of housing body 114. Facets 190a, 190c, and 190e each support an upstanding tooth 192, 194, and 196, respectively, at first end 182.

Teeth 192, 194, and 196 are received into channels 164, 166 and 168 respectively and provide the sliding engagement between shield 116 and housing body 114. Teeth 192, 194, and 198 are sized to slide within their respective channels and to pass through detents D1 and D2 so as to hold shield 116 in either an extended position or retracted position. Shield 116, in the extended position, extends about the brachytherapy seeds held within seed passageway 135 of housing body 114. Desirably, shield 116 extends about openings 132 and 134 of cartridge body 112 in the extended position. More desirably, shield 116 extends about at least a portion of fixed shield 118 when it is in the extended position. When shield 116 is in the retracted position, openings 132 and 134 will be accessible for dispensing seeds. More desirably, in a retracted position, a technician will be able to perform an assay verification and seeing how many seeds are in seed passageway 135 by referring to the counting markers on cartridge body 112. Detents D1 and D2 are provided to keep shield 116 in the extended position during shipping and handling and in the retracted position during use. The movement of shield 116 is such that the shield will be deflected in the retracted position when cartridge assembly 110 is inserted into a surgical applicator.

Typically, to load an assembly cartridge assembly 110 a technician will first load the desired number of seeds into seed passageway 135 either manually or using automated loading equipment. After ensuring the correct loading and orientation of the seeds, the technician will connect housing body 114 to cartridge body 112. Housing body 114 will already be supporting plunger 122, spring 124, and O-ring 126 so the technician would insert the first end of plunger 122 into seed passageway 135 and then bring housing body down onto cartridge body 112 such that locking tabs 142 and 144 into J-slots 170 and 172 and twist lock the components together. Spring 124 will cause the locking tabs to hold tight within the J-slots. Then shield 116 would be lowered over housing body 114 until it posses over the detents within the channels on the housing body. The technician may snap plunger 122 at score 179 so as to provide improved protection to shipping container.

Additionally, should there be any mechanical problems, or if the user decides to individually assay seeds (loose), the present invention provides for a much more efficient disassembly and reassembly due to the quick-connect feature of locking tabs 142 and 144 and J-slots 170 and 172.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A brachytherapy seed cartridge assembly comprising:
   an elongate cartridge body defining first and second transversely-opposed openings, a first open end, and an elongate seed passageway extending therebetween;
   an elongate housing body comprising a first open end securable to said first open end of said cartridge body, a second end defining a plunger aperture, and an elongate cylindrical wall extending between said first open end and said second end;
   an elongate plunger having a first end, a second end, and an elongate plunger body extending therebetween;
   a spring means acting between said second end of said housing body and said plunger so as to urge the first end of said plunger towards said first and second transversely-opposed openings of said cartridge body; and
   an elongate movable shield comprising an elongate cylindrical shield wall formed from a radiation-shielding material, said shield wall being slideably supported over said housing body so as to movable between an extended position about said seed passageway and a retracted position towards said second end of said housing body from said extended position.

2. The cartridge assembly of claim 1, wherein said shield wall is extendable to a position about said first and second transversely-opposed openings of said cartridge body.

3. The cartridge assembly of claim 1, further comprising a fixed shield supported by said cartridge body adjacent to said first and second transversely-opposing openings of said cartridge body, said fixed shield formed from a radiation-shielding material.

4. The cartridge assembly of claim 1, wherein said housing body is formed from a radiation-shielding material.

5. The cartridge assembly of claim 1, wherein said housing body and said moveable shield further comprise a plurality of cooperating teeth and channels.

6. The cartridge assembly of claim 1, wherein said housing body and said moveable shield further comprise cooperating detents and depressions so as to hold said moveable shield at each of said extended and retracted positions.

7. The cartridge assembly of claim 1, wherein said plunger body includes a weakened portion to render the plunger body frangible thereat.

8. The cartridge assembly of claim 1, wherein said cartridge body and said housing body define cooperating engagement members to allow said housing body to be attached to said cartridge body.

9. The cartridge assembly of claim 1, further comprising an elastomeric ring positioned at the second end of said plunger.

10. The cartridge assembly of claim 3, wherein said shield wall is extendable to a position about said fixed shield.

11. The cartridge assembly of claim 1, wherein said cartridge body further comprises an elongate transversely-opening access channel in fluid communication with said seed passageway, said cartridge body further comprising numerical indicia adjacent said access channel corresponding to the number of seeds loaded therein.

* * * * *